United States Patent
Richardson et al.

(10) Patent No.: US 11,360,203 B2
(45) Date of Patent: Jun. 14, 2022

(54) CLOCK OSCILLATOR DETECTION

(71) Applicant: QUALCOMM Incorporated, San Diego, CA (US)

(72) Inventors: Laurence George Richardson, Ely (GB); Christopher Church, Cambridge (GB); Jonathan Grenville Tanner, Sidmouth (GB); Magnus Sigverth Sommansson, Veberod (SE); Mayank Batra, Cambridge (GB)

(73) Assignee: QUALCOMM INCORPORATED, San Diego, CA (US)

( * ) Notice: Subject to any disclaimer, the term of this patent is extended or adjusted under 35 U.S.C. 154(b) by 185 days.

(21) Appl. No.: 16/714,259

(22) Filed: Dec. 13, 2019

(65) Prior Publication Data
US 2020/0166628 A1 May 28, 2020

Related U.S. Application Data

(63) Continuation of application No. 16/203,567, filed on Nov. 28, 2018, now Pat. No. 10,557,932.

(51) Int. Cl.
*G01S 13/56* (2006.01)
*G06F 1/10* (2006.01)
(Continued)

(52) U.S. Cl.
CPC ............... *G01S 13/56* (2013.01); *G06F 1/10* (2013.01); *H01P 1/20* (2013.01); *H01Q 1/24* (2013.01);
(Continued)

(58) Field of Classification Search
CPC ... G01S 13/56; G06F 1/10; H01P 1/20; H01Q 1/24; H03H 7/0161; H04B 7/0802
See application file for complete search history.

(56) References Cited

U.S. PATENT DOCUMENTS

| | | | | |
|---|---|---|---|---|
| 4,144,706 A | * | 3/1979 | Willis | G04G 13/02 368/12 |
| 4,570,247 A | * | 2/1986 | Walker | G08B 13/1627 340/552 |

(Continued)

FOREIGN PATENT DOCUMENTS

| | | |
|---|---|---|
| CN | 103560753 B | 4/2017 |
| CN | 207424242 U | 5/2018 |

(Continued)

OTHER PUBLICATIONS

Friedel et al: "Development of an automated unintended radiated emission (URE) radio frequency (RF) measurement system," 84th ARFTG Microwave Measurement Conference, 2014, pp. 1-6, doi: 10.1109/ARFTG.2014.7013423. (Year: 2014).*

(Continued)

*Primary Examiner* — Nay Tun
(74) *Attorney, Agent, or Firm* — Muncy, Geissler, Olds & Lowe, P.C.

(57) ABSTRACT

Motion-detection systems are often used to detect presence of humans. Such motion-detection systems are often based on passive infrared (PIR) sensors. Unfortunately, such detection systems are unable to reliably distinguish between humans and other entities such as animals and moving heat sources. To address this issue, it is proposed to detect a presence of real time clock (RTC) devices in addition to detecting the heat sources to better determine whether a detected entity is a human.

20 Claims, 5 Drawing Sheets

(51) Int. Cl.
  *H01P 1/20* (2006.01)
  *H01Q 1/24* (2006.01)
  *H03H 7/01* (2006.01)
  *H04B 7/08* (2006.01)

(52) U.S. Cl.
  CPC ......... *H03H 7/0161* (2013.01); *H04B 7/0802* (2013.01)

(56) References Cited

U.S. PATENT DOCUMENTS

| | | | | |
|---|---|---|---|---|
| 5,227,764 | A * | 7/1993 | Umemoto | G08B 13/2497 340/426.26 |
| 5,463,598 | A * | 10/1995 | Holland | G01S 5/183 367/131 |
| RE42,840 | E * | 10/2011 | Todoroki | G01S 13/56 4/304 |
| 8,063,813 | B1 * | 11/2011 | Keller | F41H 11/32 342/22 |
| 8,264,226 | B1 * | 9/2012 | Olsson | G01V 3/10 324/329 |
| 8,537,050 | B2 * | 9/2013 | Freeman | G01V 3/12 342/193 |
| 8,593,331 | B2 * | 11/2013 | Tsai | G01S 11/02 342/42 |
| 9,173,088 | B1 * | 10/2015 | Sternowski | H04W 48/04 |
| 9,285,463 | B1 * | 3/2016 | Freeman | F41H 13/0043 |
| 9,689,964 | B2 * | 6/2017 | Sarangapani | G01S 5/0226 |
| 10,557,932 | B1 | 2/2020 | Richardson et al. | |
| 2004/0106967 | A1 * | 6/2004 | Von Arx | A61N 1/37229 607/60 |
| 2004/0225439 | A1 * | 11/2004 | Gronemeyer | G04F 5/00 701/469 |
| 2005/0206516 | A1 | 9/2005 | Tsuji | |
| 2007/0026832 | A1 * | 2/2007 | Someya | G04R 20/10 455/263 |
| 2007/0286028 | A1 * | 12/2007 | Meltzer | G04R 20/10 368/47 |
| 2009/0086693 | A1 * | 4/2009 | Kennedy | H04W 48/02 370/338 |
| 2010/0034190 | A1 * | 2/2010 | Yun | H04W 56/0035 370/350 |
| 2010/0283452 | A1 * | 11/2010 | Voisine | G01R 35/04 324/96 |
| 2010/0328068 | A1 * | 12/2010 | Schreiner | G01S 13/583 340/554 |
| 2011/0050306 | A1 * | 3/2011 | Karaki | H04W 52/0287 327/160 |
| 2011/0181366 | A1 * | 7/2011 | Schoepf | H03L 7/16 331/18 |
| 2011/0267222 | A1 | 11/2011 | Craig | |
| 2012/0179812 | A1 * | 7/2012 | Keller, III | G01S 5/02 709/224 |
| 2013/0015355 | A1 | 1/2013 | Noone et al. | |
| 2014/0143469 | A1 * | 5/2014 | Tran | G06F 13/24 710/268 |
| 2014/0167766 | A1 * | 6/2014 | Olsson | G01V 3/165 324/329 |
| 2015/0091547 | A1 * | 4/2015 | Vasilev | H04K 3/822 324/76.45 |
| 2015/0241493 | A1 * | 8/2015 | Canne | G01R 29/0814 324/612 |
| 2015/0358337 | A1 * | 12/2015 | Keller | G06F 11/00 726/23 |
| 2016/0098561 | A1 * | 4/2016 | Keller | G06F 21/554 726/24 |
| 2016/0124041 | A1 * | 5/2016 | Pathak | H01L 23/576 324/629 |
| 2016/0240023 | A1 * | 8/2016 | Toivonen | H04W 4/80 |
| 2017/0042425 | A1 * | 2/2017 | Ramlall | A61B 5/0205 |
| 2018/0106897 | A1 * | 4/2018 | Shouldice | A61B 5/113 |
| 2018/0313877 | A1 * | 11/2018 | Brant | H01Q 1/36 |

FOREIGN PATENT DOCUMENTS

| | | |
|---|---|---|
| EP | 1605276 A1 | 12/2005 |
| TW | 486096 U | 5/2002 |
| TW | M273746 U | 8/2005 |

OTHER PUBLICATIONS

Slavković et al: "Computer analysis of a crystal filter with four crystal units," 2012 20th Telecommunications Forum (TELFOR), 2012, pp. 760-763, doi: 10.1109/TELFOR.2012.6419319. (Year: 2012).*

Weng et al.: "Neural network detection and identification of electronic devices based on their unintended emissions", 2005 International Symposium on Electromagnetic Compatibility, 2005. EMC 2005. (vol. 1, pp. 245-249 vol. 1), doi: 10.1109/ISEMC.2005.1513508 [retrieved on Aug. 5, 2021] (Year: 2005).*

Stagnet et al. "A Practical Superheterodyne-Receiver Detector Using Stimulated Emissions". Publication Date: Apr. 1, 2011 IEEE Transactions on Instrumentation and Measurement (vol. 60, Issue: 4, pp. 1461-1468), doi, 10.1109/TIM.2010.2101330 (Year: 2011).*

International Search Report and Written Opinion—PCT/US2019/058448—ISA/EPO—dated Apr. 15, 2020.

Partial International Search Report—PCT/US2019/058448—ISA/EPO—dated Feb. 4, 2020.

Taiwan Search Report—TW108139017—TIPO—dated Aug. 13, 2020.

Teixeira T., "A Survey of Human-Sensing: Methods for Detecting Presence, Count, Location, Track, and Identity", Sep. 1, 2010 (Sep. 1, 2010), XP055101195, pp. 1-35, Retrieved from the Internet: URL: http://www.cse.buffalo.edu/~wenyaoxu/courses/cse741/papers/human_sensing.pdf, [retrieved on Feb. 10, 2014], Sections: I. Introduction, 4. Survey of existing approaches, 4.1.1 Binary sensors, 4.1.3 Radio, Ultrasound, Laser, 4.2.2 Environment Recognition, 4.3 Sensor Fusion Approaches.

* cited by examiner

CLOCK OSCILLATOR DETECTION

CROSS-REFERENCE TO RELATED APPLICATIONS

The present application for patent is a continuation of U.S. application Ser. No. 16/203,567, entitled "CLOCK OSCILLATOR DETECTION" filed Nov. 28, 2018, assigned to the assignee hereof, and expressly incorporated herein by reference in its entirety.

FIELD OF DISCLOSURE

One or more aspects of the present disclosure generally relate to radio wave detection, and in particular, to clock oscillator detection.

BACKGROUND

Motion-detection systems are often used to detect presence of humans. Such motion-detection systems are often based on passive infrared (PIR) sensors. Unfortunately, such detection systems are unable to reliably distinguish between humans and other entities such as animals and other moving heat sources.

SUMMARY

This summary identifies features of some example aspects, and is not an exclusive or exhaustive description of the disclosed subject matter. Whether features or aspects are included in, or omitted from this summary is not intended as indicative of relative importance of such features. Additional features and aspects are described, and will become apparent to persons skilled in the art upon reading the following detailed description and viewing the drawings that form a part thereof.

An exemplary oscillator detector is disclosed. The oscillator detector may comprise an antenna, a band pass filter, a signal processor, and a control circuit. The antenna may be configured to receive radio signals, which may include real time clock (RTC) emissions. The RTC emissions may be radio waves emitted by an RTC device at an RTC frequency. The band pass filter may be configured to filter the radio signals received by the antenna and output filtered radio signals. The band pass filter may be tuned to the RTC frequency. The signal processor may be configured to process the filtered radio signals and output radio signal data. The control circuit may be configured to detect the RTC device based on the radio signal data.

An exemplary detection system is disclosed. The detection system may comprise a motion detector, an oscillator detector, and a controller. The motion detector may be configured to detect an entity. The oscillator detector may be configured to detect a real time clock (RTC) device operating at an RTC frequency. The controller may be configured to determine whether the entity is human or not based on whether or not the motion detector detects the entity and whether or not the oscillator detector detects the RTC device.

An exemplary method is disclosed. The method may comprise detecting, using a motion detector of a detection system, an entity. The method may also comprise detecting, using an oscillator detector of the detection system, a real time clock (RTC) device operating at an RTC frequency. The method may further comprise determining, using a controller of the detection system, whether the entity is human or not based on whether or not the entity is detected and whether or not the RTC device is detected.

Another exemplary oscillator detector is disclosed. The oscillator detector may comprise means for receiving radio signals, means for band pass filtering, means for signal processing, and means for detecting. The means for receiving radio signals may receive radio signals, which may include real time clock (RTC) emissions. The RTC emissions may be radio waves emitted by an RTC device at an RTC frequency. The means for band pass filtering may filter the radio signals received by the means for receiving radio signals. The means for band pass filtering may also output filtered radio signals. The means for band pass filtering may be tuned to the RTC frequency. The means for signal processing may process the filtered radio signals and output radio signal data. The means for detecting may detect the RTC device based on the radio signal data.

BRIEF DESCRIPTION OF THE DRAWINGS

The accompanying drawings are presented to aid in the description of examples of one or more aspects of the disclosed subject matter and are provided solely for illustration of the examples and not limitation thereof.

DETAILED DESCRIPTION

Figure 1:
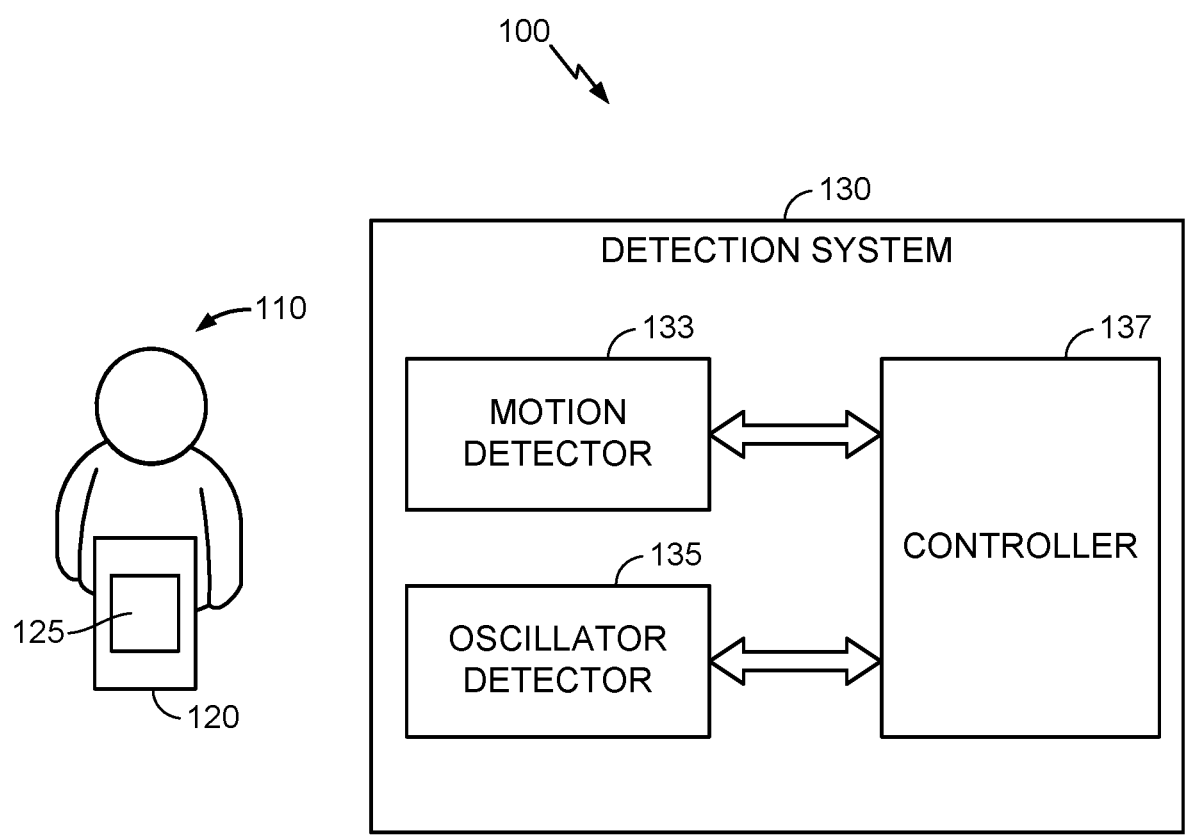
FIG. 1 illustrates an example scenario in which a detection system is used to detect whether or not an entity is a human.

Aspects of the subject matter are provided in the following description and related drawings directed to specific examples of the disclosed subject matter. Alternates may be devised without departing from the scope of the disclosed subject matter. Additionally, well-known elements will not be described in detail or will be omitted so as not to obscure the relevant details.

The word "exemplary" is used herein to mean "serving as an example, instance, or illustration." Any embodiment described herein as "exemplary" is not necessarily to be construed as preferred or advantageous over other embodiments. Likewise, the term "embodiments" does not require that all embodiments of the disclosed subject matter include the discussed feature, advantage or mode of operation.

The terminology used herein is for the purpose of describing particular examples only and is not intended to be limiting. As used herein, the singular forms "a", "an" and "the" are intended to include the plural forms as well, unless the context clearly indicates otherwise. It will be further understood that the terms "comprises", "comprising", "includes" and/or "including", when used herein, specify the presence of stated features, integers, processes, operations, elements, and/or components, but do not preclude the presence or addition of one or more other features, integers, processes, operations, elements, components, and/or groups thereof.

Further, many examples are described in terms of sequences of actions to be performed by, for example, elements of a computing device. It will be recognized that various actions described herein can be performed by specific circuits (e.g., application specific integrated circuits (ASICs)), by program instructions being executed by one or more processors, or by a combination of both. Additionally, these sequence of actions described herein can be considered to be embodied entirely within any form of computer-readable storage medium having stored therein a corresponding set of computer instructions that upon execution would cause an associated processor to perform the functionality described herein. Thus, the various aspects may be embodied in a number of different forms, all of which have been contemplated to be within the scope of the claimed subject matter. In addition, for each of the examples described herein, the corresponding form of any such examples may be described herein as, for example, "logic configured to" perform the described action.

Recall from above that typical motion-detection systems designed to detect the presence of a human, such as those based on passive infrared (PIR) devices, are unable to reliably distinguish between humans and other heated objects such as animals and other moving heat sources (e.g., vent releasing heated air).

One aspect that does typically distinguish humans from animals and other heated objects is that humans tend to be equipped with electronic devices such as digital watches and smart phones. Thus, to address one or more issues associated with the conventional detection systems, it is proposed to detect presence of electronic devices. In particular, it is proposed to detect the presence of clock oscillators in real time clock (RTC) devices. Many electronic devices contain at least one oscillator which is used as a timing source for an RTC or other purposes. Many portable devices that contain RTCs are in existence. Such portable devices are often body-worn or otherwise carried around with the person.

Convention is to use 32,768 Hz ($2^{15}$ Hz) oscillators in these RTCs. This frequency can be divided by 2 to the power of 15 to get one tick per second. Dividing by 2 to the power of anything is simple to implement in digital gates, and thus has become popular. Owing to the convenience of dividing the number 32,768 in inexpensive digital circuitry, accurate oscillators running at 32,768 Hz have become ubiquitous. The end result is that there are billions of electronic devices that use RTCs with the same 32,768 Hz frequency.

Economies of scale have made the quartz crystals that are used as the basis of such oscillators extremely inexpensive, effectively establishing a de facto frequency standard of 32,768 Hz. All electrical oscillators generate electromagnetic emissions to some degree, whether intentional or unintentional. RTC devices with 32,768 Hz oscillators are rarely screened to prevent electromagnetic emissions. This is because the 32,768 Hz frequency has a very large separation from the frequencies typically used for radio communication.

In an aspect, a sensitive oscillator detector, which may be a radio frequency detector tuned to the RTC frequency (e.g., 32,768 Hz), may be used to detect the proximity of an electronic device containing such an oscillator. Since there are more and more electronic devices that are body-worn or carried with the person, detection of a radio signal at the RTC frequency nearby can be used to detect that a human has approached the oscillator detector.

In an aspect, an oscillator detector may be combined with a motion detector as illustrated in FIG. 1, which illustrates a scenario 100 in which a detection system 130 may be used to detect whether a human is in proximity of the detection system 130. In this instance, an entity 110 (e.g., a human) is illustrated as having a portable device 120 that incorporates an RTC device 125. The portable device 120 may be a body-worn device. While not illustrated, it is of course possible that there may be multiple portable devices 120 with RTC devices 125 incorporated therein.

The detection system 130 may comprise a motion detector 133, an oscillator detector 135, and a controller 137. An example of the motion detector 133 may be an infrared (IR) based sensor such as a PIR sensor. The motion detector 133 may be configured to detect an entity 110 in proximity to the detection system 130. For example, the motion detector 133 may detect the entity 110 when the entity 110 is within a detection range of the motion detector 133. Alternatively or in addition thereto, the motion detector 133 may be configured to provide the controller 137 with motion data, from which the controller 137 may determine whether the entity 110 has been detected.

The oscillator detector 135 may be configured to detect an RTC device 125 when the RTC device 125 is in proximity to the detection system 130. For example, the oscillator detector 135 may detect the RTC device 125 when the RTC device 125 is within a detection range of the oscillator detector 135. Alternatively or in addition thereto, the oscillator detector 135 may be configured to provide the controller 137 with oscillator data, from which the controller 137 may determine whether the RTC device 125 has been detected.

In an aspect, the oscillator detector 135 may detect presence or absence of RTC emissions. In this context, RTC emissions may be viewed as radio waves emitted by the RTC device 125 at an RTC frequency. The RTC frequency may be a fixed frequency of $2^N$ Hz, in which N is a non-negative integer, i.e., N≥0. When N=15, the RTC frequency is 32,768 Hz. Details of the oscillator detector 135 will be presented further below.

The controller 137 may be a decision-making element that evaluates signals from both the motion detector 133 and the oscillator detector 135 to determine whether a human is in proximity. For example, the controller 137 may be configured to determine whether or not the entity 110 is human based on whether or not the entity 110 has been detected (by the motion detector 133 itself or by the controller 137 from the motion data provided by the motion detector 133) and whether or not the RTC device 125 has been detected (by the oscillator detector 135 itself or by the controller 137 from the oscillator data provided by the oscillator detector 135). For example, the controller 137 may determine that the entity 110 is human when the entity 110 and the RTC device 125 have both been detected.

With respect to the detection system 130 illustrated in FIG. 1, the following will be assumed in the discussion that follows. First, it will be assumed that the motion detector 133 is configured to detect the entity 110. Second, it will be assumed that the oscillator detector 135 is configured to detect the RTC device 125. However, it is relatively straight forward to contemplate an alternative detection system in which the controller 137 processes one or both of the motion data and the oscillator data to make similar determinations. Therefore, detailed descriptions of such alternative detection systems 130 will be omitted.

Referring back to the detection system 130 illustrated in FIG. 1, the controller 137 may determine that the entity 110 is human when it is determined that the entity 110 and the RTC device 125 are in proximity of the detection system 130. That is, controller 137 may determine that the entity 110 is human when the motion detector 133 detects the entity 110 and when the oscillator detector 135 detects the RTC device 125. By considering the detection results from both the motion detector 133 and the oscillator detector 135, greater reliability may be achieved than would be achieved by relying upon a single type of detection of either type.

Reliability may be enhanced if the detection results of the motion detector 133 and the oscillator detector 135 verify each other. For example, the motion detector 133 may be configured to determine a distance of the entity 110 (referred to as "entity distance" for convenience), and the oscillator detector 135 may be configured to determine a distance of the RTC device 125 (referred to as "RTC device distance" for convenience). The entity and RTC device distances may be distances from the detection system 130. The controller 137 may be configured to determine that the entity 110 is human when the entity distance and the RTC device distance are within a threshold distance difference of each other. The threshold distance difference may be predetermined. Alternatively, the threshold distance difference may be configured during operation. The threshold distance difference may be set to be within margins of measurement errors in distances of the motion detector 133 and the oscillator detector 135.

As another example, the motion detector 133 may be configured to determine a direction of the entity 110 (referred to as "entity direction" for convenience), and the oscillator detector 135 may be configured to determine a direction of the RTC device 125 (referred to as "RTC device direction" for convenience). The entity and RTC device directions may be directions in relation to the detection system 130. The controller 137 may be configured to determine that the entity 110 is human when the entity direction and the RTC device direction are within a threshold direction difference of each other. The threshold direction difference may be predetermined. Alternatively, the threshold direction difference may be configured during operation. The threshold direction difference may be set to be within margins of measurement errors in directions of the motion detector 133 and the oscillator detector 135.

As a further example, both direction and distance may be combined. That is, the motion detector 133 may be configured to determine a location (e.g., combination of direction and distance) of the entity 110 (referred to as "entity location" for convenience), and the oscillator detector 135 may be configured to determine a location of the RTC device 125 (referred to as "RTC device location" for convenience). The entity and RTC device locations may be locations relative to the detection system 130. The controller 137 may be configured to determine that the entity 110 is human when the entity location and the RTC device location are within a threshold location difference of each other. The threshold location difference may be predetermined. Alternatively, the threshold location difference may be configured during operation. The threshold location difference may be set to be within margins of measurement errors in distances and directions of the motion detector 133 and the oscillator detector 135.

The controller 137 may advantageously use the direction detection capabilities of the motion detector 133 and/or the oscillator detector 135. For example, when the oscillator detector 135 detects the RTC device direction, the controller 137 may be configured to orient the motion detector 133 in the RTC device direction. Alternatively or in addition thereto, when the motion detector 133 detects the entity direction, the controller 137 may be configured to orient the oscillator detector 135 in the entity direction.

Figure 2:
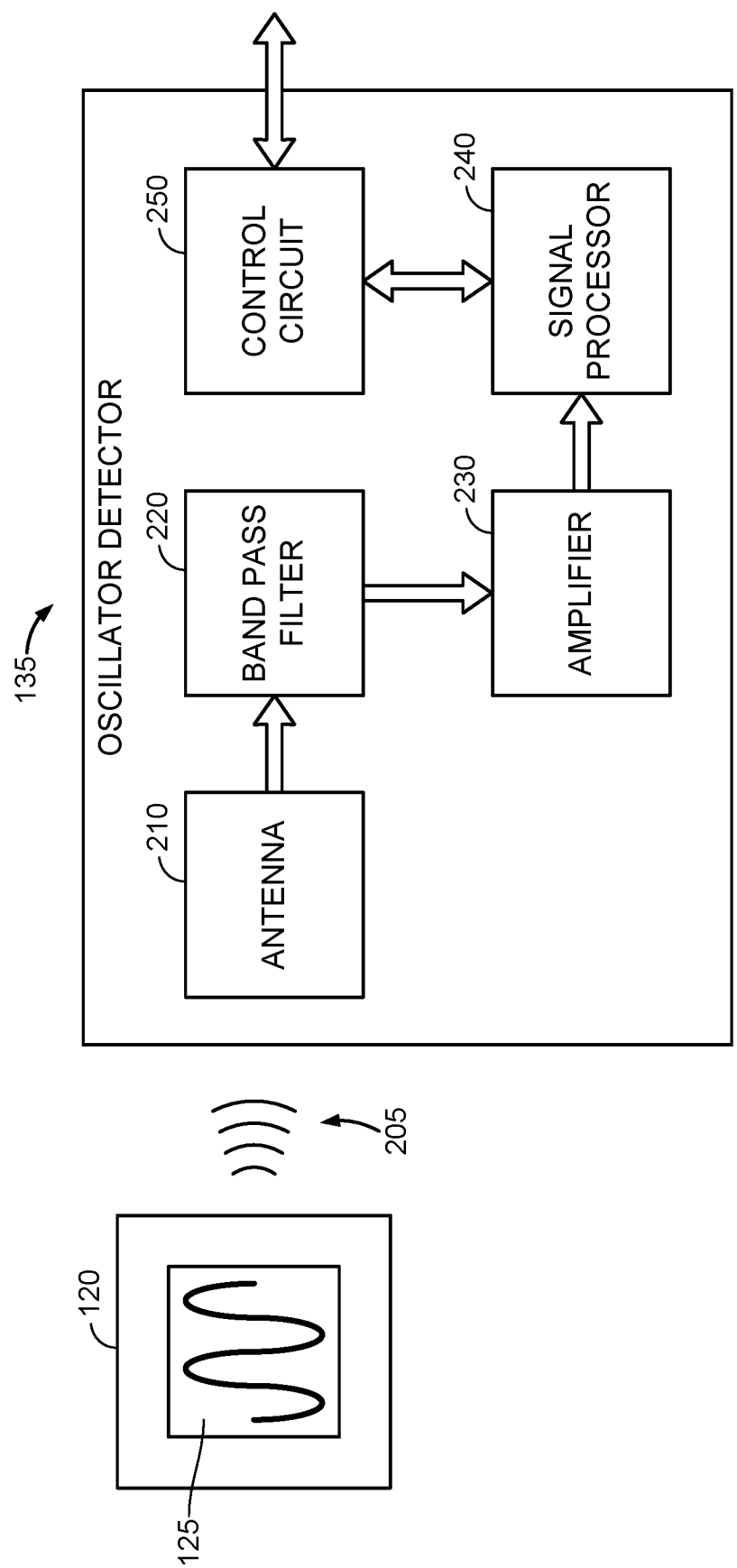
FIG. 2 illustrates an example scenario in which an oscillator detector is used to detect a real time clock device.

FIG. 2 illustrates an example scenario in which the oscillator detector 135 may be used to detect the RTC device 125. As indicated above, the RTC device 125 may be incorporated in the portable device 120. The RTC device 125 is illustrated as emitting RTC emissions 205 which are radio waves generated from the operation of the RTC device 125. In general, the RTC emissions 205 are unintended emissions. They are generated as a byproduct of the RTC device 125 operating. However, since radio signals at the RTC frequency—e.g., 32,768 Hz—are vastly different from frequencies normally used for wireless communication, the RTC emissions 205 do not normally interfere with wireless communications. Therefore, it is typical that no special measures are taken to screen the RTC emissions 205.

The oscillator detector 135 may comprise an antenna 210, a band pass filter 220, an amplifier 230, a signal processor 240, and a control circuit 250. The antenna 210 may be configured to receive radio signals including the RTC emissions 205 from the RTC device 125. As indicated above, the RTC emissions 205 may be described as radio waves emitted by the RTC device 125 at the RTC frequency (e.g., $2^{15}$ Hz). While the singular form "antenna" is used, it should be noted that the antenna 210 may be implemented in a variety of forms. The antenna 210 may comprise any number (one or more) physical antennas. The antenna 210 may also be directional to enable determining the originating direction of the RTC emissions 205.

The band pass filter 220 may be configured to band pass filter the radio signals received by the antenna 210 and output filtered radio signals. The band pass filter 220 may be tuned to the RTC frequency (e.g., $2^N$ Hz, N≥0). In an embodiment, the band pass filter 220 may be a narrow bandwidth crystal ladder filter comprising a plurality of RTC frequency crystals that vibrate at the RTC frequency, e.g., with a nominal resonant frequency of 32,768 Hz. In other words, the plurality of crystals may be arranged in a filter topology that exhibits a peak response at the RTC frequency. Due to the widespread nature of RTC devices, very accurate crystals of this frequency are widely available and inexpensive. As a result, the bandwidth of the band pass filter 220 can be made very narrow. For example, a bandwidth as narrow as 2.0 Hz or less is achievable with a typical ladder filter comprising four suitably matched crystals. This means that the band pass filter 220 can be finely tuned to detect the RTC frequency with a very high Q factor. For example, a Q factor of 16,000 or more is achievable with a typical ladder filter.

In an aspect, the signal processor 240 may process the filtered radio signals from the band pass filter 220 and output radio signal data. But in another aspect, the amplifier 230 may be configured to amplify the filtered radio signals from the band pass filter 220. The signal processor 240 in turn may process the amplified filtered radio signals from the amplifier 230 to output the radio signal data. It is mentioned above that the RTC emissions 205 from the RTC device 125 are not screened or shielded from being transmitted. Nonetheless, these unintended transmissions can be weak transmissions. Therefore, the amplifier 230 can enhance the sensitivity of the oscillator detector 135 as a whole.

The control circuit 250 may be configured to communicate with devices external to the oscillator detector 135 (e.g., with controller 137). In one aspect, the control circuit 250 may forward the radio signal data to the controller 137 as oscillator data.

But in another aspect, the control circuit 250 may be configured to detect the RTC device 125 based on the radio signal data from the signal processor 240. For example, when the radio signal data indicates that a strength level of the RTC emissions 205 is higher than an RTC threshold level, the control circuit 250 may determine that the RTC device 125 has been detected.

The RTC threshold level may be set, e.g., by the control circuit 250 and/or the controller 137, in consideration of ambient levels dependent on electrical noise and sources of RTC emissions 205 in the operation environment of the oscillator detector 135. For example, there may be one or more RTC devices 125 within the detection system 130 (not shown). In other words, there may be one or more "internal" RTC devices 125. Also, the operation environment of the detection system 130 may include devices that incorporate RTC devices (not shown). The RTC threshold level may be set to account for these "expected" RTC emissions 205. The RTC device 125 to be detected then would cause the RTC emissions 205 to increase above the RTC threshold level in which the expected RTC emissions 205 have been taken into account. In an embodiment, some or all of the internal RTC devices 125 may be shielded or otherwise screened. In this instance, the RTC threshold level may be lowered accordingly.

The RTC emissions level may be used determine the distance of the RTC device 125. In particular, the control circuit 250 may be configured to determine a distance between the RTC device 125 and the oscillator detector 135 (or between the RTC device 125 and the detection system 130) based on the radio signal data. Also, a change in the RTC emissions level may be used to detect a direction of motion, e.g., moving toward/away from the oscillator detector 135/detection system 130.

In some circumstances, the strength of the RTC emissions 205 level may be used to enable an action. For example, if a human presents a portable device 120 (e.g., quartz watch, cell phone, etc.) that incorporates the RTC device 125 to the detection system 130, then the control circuit 250 or the controller 137 may enable an action such as starting a machinery, operating a door, and so on. When the RTC device 125 is purposefully presented, the strength of the RTC emissions 205 should be fairly strong. Thus, in an aspect, the control circuit 250 or the controller 137 may initiate the action when the strength level of the RTC emissions 205 is higher than an action threshold level. The action threshold level should be significantly higher than the RTC threshold level, e.g., by 10 dB or more.

When the antenna 210 is a directional antenna, then the control circuit 250 may be able to determine the lateral (left/right) and vertical (up/down) direction of the RTC device 125 in addition to determining the distance. That is, the control circuit 250 may be configured to detect the location of the RTC device 125. A logical extension is that the control circuit 250 may also be configured to determine the motion of the RTC device 125 in all directions. Such capabilities may be very useful in emergency situations such as detecting people buried in an avalanche.

Figure 3:
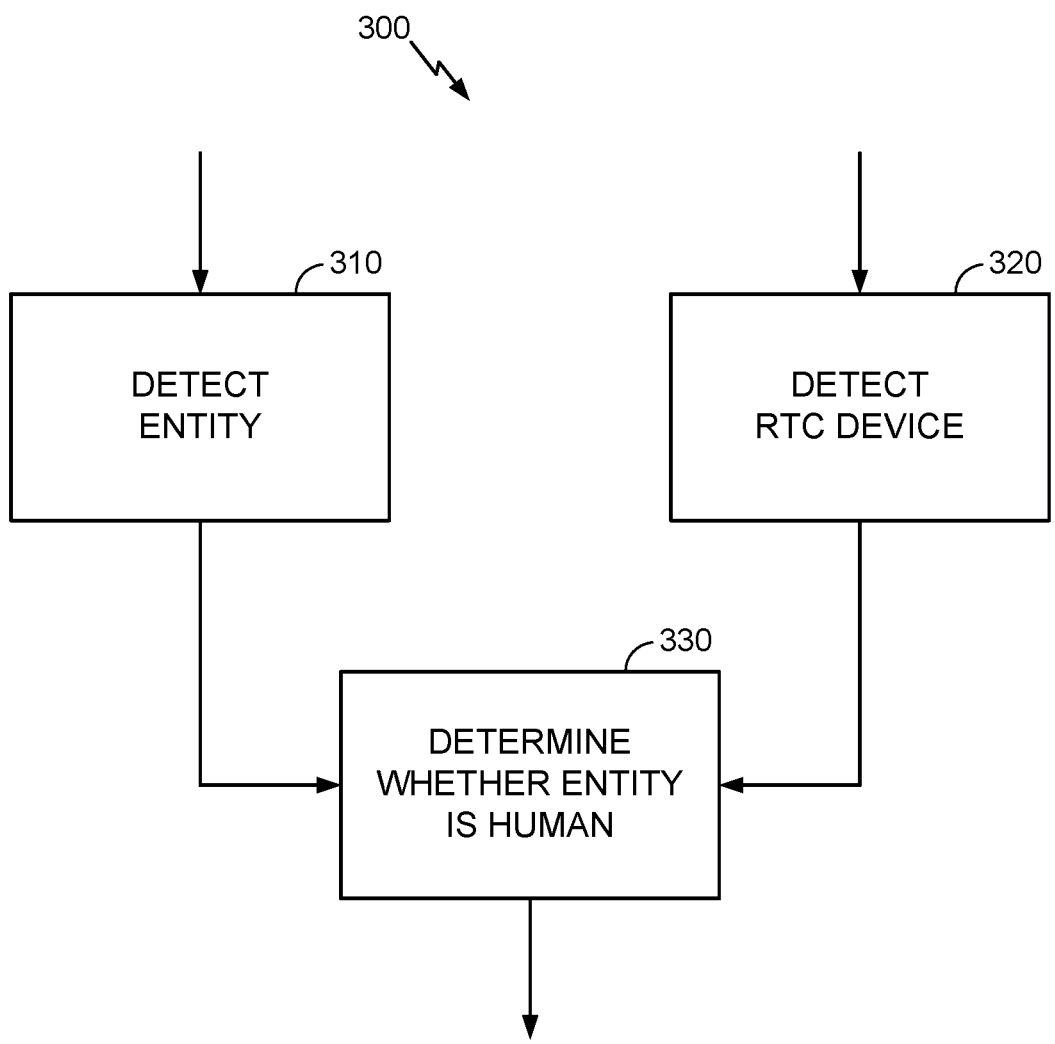
FIG. 3 illustrates a flow chart of an example method performed by a detection system.

FIG. 3 illustrates a flow chart of an example method 300 performed by a detection system such as the detection system 130. At 310, the motion detector 133 may detect the entity 110 when the entity 110 is in proximity of the detection system 130. At 320, the oscillator detector 135 may detect the RTC device 125 when the RTC device 125 is in proximity of the detection system 130.

Figure 4:
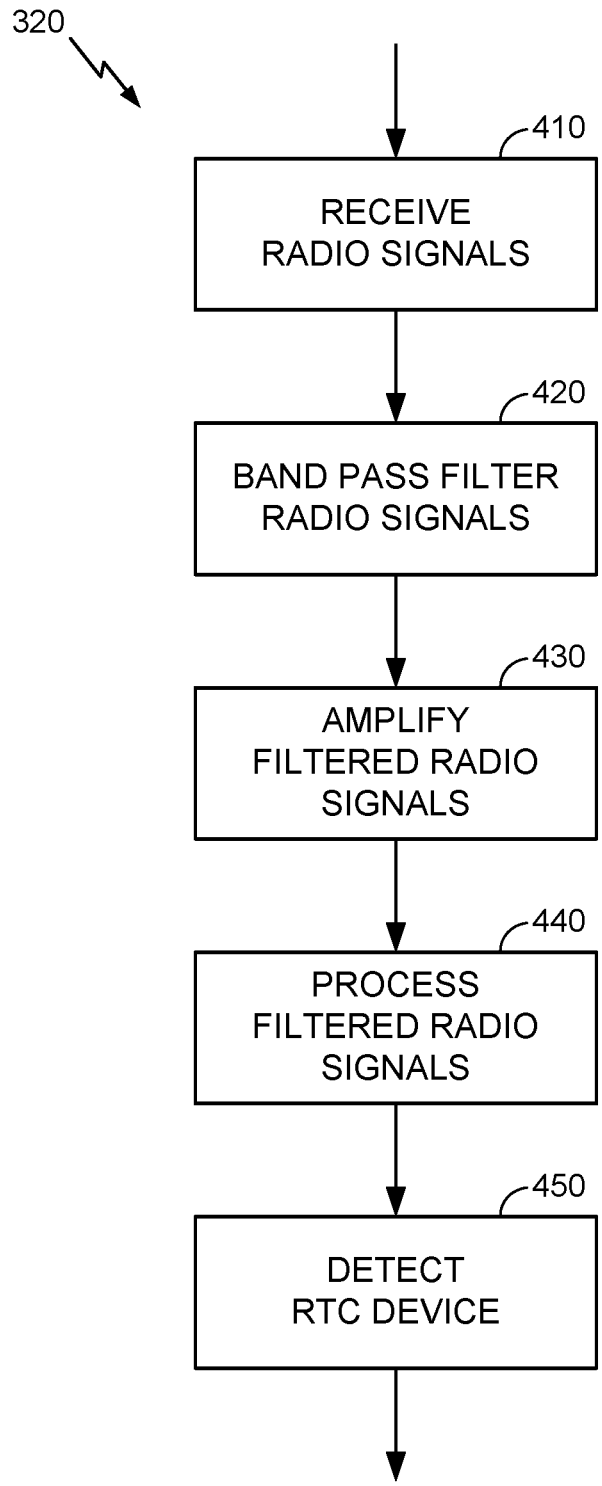
FIG. 4 illustrates a flow chart of an example process performed by an oscillator detector to detect a real time clock device.

FIG. 4 illustrates a flow chart of an example process performed by the oscillator detector 135 to implement 320. At 410, the antenna 210 may receive radio signals including the RTC emissions 205 from the RTC device 125. At 420, the band pass filter 220 may band pass filter the radio signals received by the antenna 210 and output filtered radio signals. At 430, the amplifier 230 may amplify the filtered radio signals from the band pass filter 220. At 440, the signal processor 240 may process the filtered radio signals (whether amplified or not) and output radio signal data. At 450, the control circuit 250 may detect the RTC device 125 based on the radio signal data.

Referring back to FIG. 3, at 330, the controller 137 may determine whether the entity 110 is human or not based on whether or not the entity 110 is detected and whether or not the RTC device 125 is detected. For example, at 330, it may be determined that the entity 110 is human when the entity 110 is detected and when the RTC device 125 is detected.

Recall that in an aspect, the motion detector 133 can determine the entity distance when the entity 110 is detected, and the oscillator detector 135 can determine the RTC device distance when the RTC device 125 is detected. Then at 330, it may be determined that the entity 110 is human when the entity distance and the RTC device distance are within the threshold distance difference of each other.

Also recall that in another aspect, the motion detector 133 can determine the entity direction when the entity 110 is detected, and the oscillator detector 135 can determine the RTC device direction when the RTC device 125 is detected. Then at 330, it may be determined that the entity 110 is human when the entity direction and the RTC device direction are within the threshold direction difference of each other.

Of course, distance and direction may be combined. That is, in yet another aspect, the motion detector 133 can determine the entity location when the entity 110 is detected, and the oscillator detector 135 can determine the RTC device location when the RTC device 125 is detected. Then at 330, it may be determined that the entity 110 is human when the entity location and the RTC device location are within the threshold direction difference of each other.

It should be noted that not all illustrated blocks of FIGS. 3 and 4 need be performed, i.e., some blocks may be optional. Also, the numerical references to the blocks in these figures should not be taken as requiring that the blocks should be performed in a certain order. Indeed, some blocks may be performed concurrently.

Figure 5:
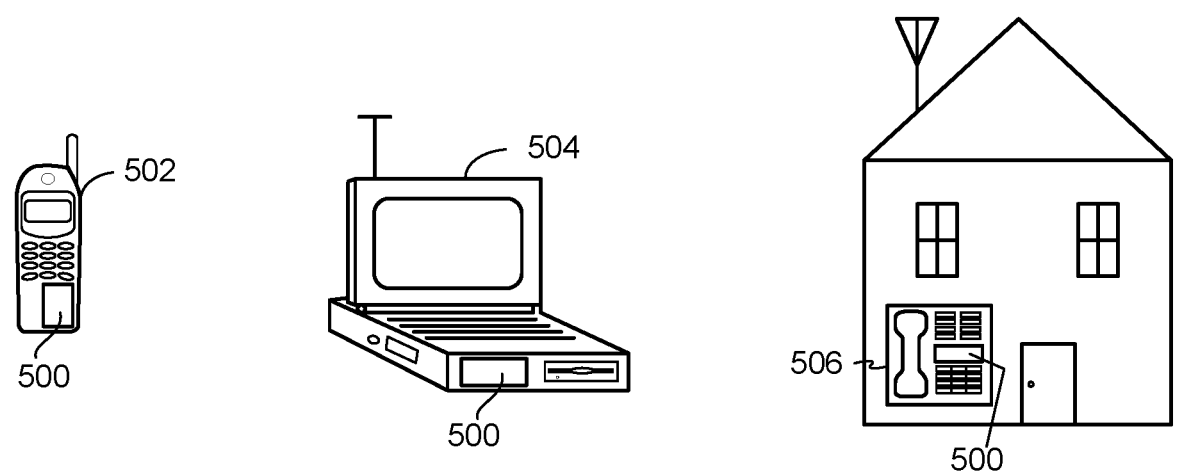
FIG. 5 illustrates examples of devices with an apparatus integrated therein.

FIG. 5 illustrates various electronic devices that may be integrated with the aforementioned oscillator detector 135 illustrated in FIG. 2 or the detection system 130 illustrated in FIG. 1. For example, a mobile phone device 502, a laptop computer device 504, a terminal device 506 as well as security devices that incorporate the oscillator detector 135/the detection system 130 as described herein may include an apparatus 500. The apparatus 500 may be a standalone device, such as a sensor, a fixed sensor, an IoT (Internet of Things) device, etc. The devices 502, 504, 506 illustrated in FIG. 5 are merely exemplary. Other electronic devices may also feature the apparatus 500 including, but not limited to, a group of devices (e.g., electronic devices) that includes security devices, mobile devices, hand-held personal communication systems (PCS) units, portable data units such as personal digital assistants, global positioning system (GPS) enabled devices, navigation devices, set top boxes, music players, video players, entertainment units, fixed location data units such as meter reading equipment, communications devices, smartphones, tablet computers, computers, wearable devices, servers, routers, electronic devices implemented in automotive vehicles (e.g., autonomous vehicles), or any combination thereof.

Those of skill in the art will appreciate that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Further, those of skill in the art will appreciate that the various illustrative logical blocks, modules, circuits, and algorithms described in connection with the examples disclosed herein may be implemented as electronic hardware, computer software, or combinations of both. To clearly illustrate this interchangeability of hardware and software, various illustrative components, blocks, modules, circuits, and methods have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The methods, sequences and/or algorithms described in connection with the examples disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled with the processor such that the processor can read information from, and write information to, the storage medium. In the alternative, the storage medium may be integral to the processor.

Accordingly, an aspect can include a computer-readable media embodying any of the devices described above. Accordingly, the scope of the disclosed subject matter is not limited to illustrated examples and any means for performing the functionality described herein are included.

While the foregoing disclosure shows illustrative examples, it should be noted that various changes and modifications could be made herein without departing from the scope of the disclosed subject matter as defined by the appended claims. The functions, processes and/or actions of the method claims in accordance with the examples described herein need not be performed in any particular order. Furthermore, although elements of the disclosed subject matter may be described or claimed in the singular, the plural is contemplated unless limitation to the singular is explicitly stated.

What is claimed is:

1. An oscillator detector, comprising:
    an antenna configured to receive radio signals, the radio signals including real time clock (RTC) emissions, the RTC emissions being radio waves emitted by a RTC device at a RTC frequency;
    a band pass filter configured to band pass filter the radio signals received by the antenna and output filtered radio signals, the band pass filter being tuned to the RTC frequency;
    a signal processor configured to process the filtered radio signals and output radio signal data; and
    a control circuit configured to detect the RTC device based on the radio signal data,
    wherein the control circuit is configured to determine that the RTC device has been detected when a strength level of the RTC emissions is higher than a RTC threshold level, the RTC threshold level being set in consideration of RTC emissions from one or more internal RTC devices within a detection system incorporating the oscillator detector.

2. The oscillator detector of claim 1, wherein the RTC frequency is a fixed frequency of $2^N$ Hz, N being a non-negative integer.

3. The oscillator detector of claim 2, wherein N=15.

4. The oscillator detector of claim 1, wherein the band pass filter is a crystal ladder filter comprising a plurality of crystals arranged in a filter topology that exhibits a peak response at the RTC frequency.

5. The oscillator detector of claim 1, further comprising:
    an amplifier configured to amplify the filtered radio signals,
    wherein the signal processor is configured to process the amplified filtered radio signals to output the radio signal data.

6. The oscillator detector of claim 1, wherein the control circuit configured to determine a distance of the RTC device from the oscillator detector based on the radio signal data.

7. The oscillator detector of claim 1,
    wherein the antenna is a directional antenna, and
    wherein the control circuit configured to determine, based on the radio signal data,
        a distance between the RTC device and the oscillator detector, or
        a direction of the RTC device relative to the oscillator detector, or both.

8. The oscillator detector of claim 1, wherein the RTC device is incorporated in a portable device.

9. The oscillator detector of claim 8, wherein the portable device is a body-worn device.

10. The oscillator detector of claim 1, wherein the oscillator detector is incorporated into a device selected from a group consisting of security devices, mobile devices, handheld personal communication systems (PCS) units, portable data units, global positioning system (GPS) enabled devices, navigation devices, set top boxes, music players, video players, entertainment units, fixed location data units, communications devices, smartphones, tablet computers, computers, wearable devices, servers, routers, electronic devices implemented in automotive vehicles, or any combination thereof.

11. The oscillator detector of claim 1, wherein the oscillator detector is incorporated into a detection system that is configured to
    detect an entity using an entity detector, and
    determine whether the entity is human or not based on whether or not the oscillator detector detects the RTC device.

12. The oscillator detector of claim 1, wherein a bandwidth of the band pass filter is 2 Hz or less.

13. The oscillator detector of claim 1, wherein a Q factor of the band pass filter is 16,000 or greater.

14. A method of an oscillator detector, the method comprising:
    receiving, via an antenna, radio signals including real time clock (RTC) emissions, the RTC emissions being radio waves emitted by a RTC device at a RTC frequency;
    filtering, using a band pass filter tuned to the RTC frequency, the radio signals received by the antenna to output filtered radio signals;
    processing, using a signal processor, the filtered radio signals to output radio signal data; and
    detecting, using a control circuit, the RTC device based on the radio signal data, wherein it is determined that the RTC device has been detected when a strength level of the RTC emissions is higher than a RTC threshold level, the RTC threshold level being set in consideration of RTC emissions from one or more internal RTC devices within a detection system incorporating the oscillator detector.

15. The method of claim 14, wherein the RTC frequency is a fixed frequency of $2^N$ Hz, N being a non-negative integer.

16. The method of claim 14, further comprising:
amplifying, using an amplifier, the filtered radio signals to output amplified filtered radio signals,
wherein processing the filtered radio signals comprises processing, using the signal processor, the amplified filtered radio signals to output the radio signal data.

17. The method of claim 14, further comprising:
determining, using the control circuit, a distance of the RTC device from the oscillator detector based on the radio signal data.

18. The method of claim 14,
wherein the antenna is a directional antenna, and
wherein the method further comprises:
    determining, using the control circuit, a distance of the RTC device from the oscillator detector based on the radio signal data, and/or
    determining, using the control circuit, a direction of the RTC device relative to the oscillator detector based on the radio signal data.

19. An oscillator detector, comprising:
means for receiving radio signals, the radio signals including real time clock (RTC) emissions, the RTC emissions being radio waves emitted by a RTC device at a RTC frequency;
means for band pass filtering the radio signals received by the means for receiving the radio signals, the means for band pass filtering outputting filtered radio signals, the means for band pass filtering being tuned to the RTC frequency;
means for signal processing the filtered radio signals, the means for signal processing outputting radio signal data; and
means for detecting the RTC device based on the radio signal data,
wherein the means for detecting determines that the RTC device has been detected when a strength level of the RTC emissions is higher than a RTC threshold level, the RTC threshold level being set in consideration of RTC emissions from one or more internal RTC devices within a detection system incorporating the oscillator detector.

20. The oscillator detector of claim 19, wherein the oscillator detector is incorporated into a detection system that is configured to
detect an entity using means for detecting the entity, and
determine whether the entity is human or not based on whether or not the oscillator detector detects the RTC device.

* * * * *